US009848767B2

(12) United States Patent
Miyashita et al.

(10) Patent No.: US 9,848,767 B2
(45) Date of Patent: Dec. 26, 2017

(54) OPHTHALMOLOGICAL APPARATUS

(71) Applicant: Kabushiki Kaisha Topcon, Itabashi-ku (JP)

(72) Inventors: Kenji Miyashita, Itabashi-ku (JP); Jun Sakai, Itabashi-ku (JP)

(73) Assignee: Kabushiki Kaisha Topcon, Itabashi-ku (JP)

( * ) Notice: Subject to any disclaimer, the term of this patent is extended or adjusted under 35 U.S.C. 154(b) by 73 days.

(21) Appl. No.: 14/941,951

(22) Filed: Nov. 16, 2015

(65) Prior Publication Data

US 2016/0143523 A1 May 26, 2016

(30) Foreign Application Priority Data

Nov. 26, 2014 (JP) .................. 2014-238988

(51) Int. Cl.
*A61B 3/00* (2006.01)
*A61B 3/11* (2006.01)
*A61B 3/12* (2006.01)
*A61B 3/14* (2006.01)

(52) U.S. Cl.
CPC .......... *A61B 3/0091* (2013.01); *A61B 3/0025* (2013.01); *A61B 3/112* (2013.01); *A61B 3/1241* (2013.01); *A61B 3/14* (2013.01)

(58) Field of Classification Search
CPC .... A61B 3/12; A61B 3/14; A61B 3/15; A61B 3/112; A61B 3/1208; A61B 3/117; A61B 3/152; A61B 3/1241; A61B 3/154; A61B 3/145; A61B 3/00; A61B 3/0091; A61B 3/0025; A61B 3/0058; A61B 3/0083; G01B 9/02; G01B 11/02

USPC ....... 351/206, 205, 208, 210, 211, 212, 214, 351/221, 238, 246; 600/316, 318, 319, 600/425, 476; 356/511, 479
See application file for complete search history.

(56) References Cited

U.S. PATENT DOCUMENTS

2006/0187462 A1* 8/2006 Srinivasan ............. A61B 3/102
356/479
2008/0239240 A1* 10/2008 Tsukada ................. A61B 3/102
351/211
2010/0149489 A1 6/2010 Kikawa et al.
(Continued)

FOREIGN PATENT DOCUMENTS

JP 2008-289579 12/2008
JP 2013-248376 12/2013

*Primary Examiner* — Jie Lei
(74) *Attorney, Agent, or Firm* — Oblon, McClelland, Maier & Neustadt, L.L.P.

(57) ABSTRACT

An ophthalmological apparatus includes a photographing mode selection processor that selects any one of a plurality of photographing modes including a color photographing mode and a fluorescent photographing mode, a photographic optical system that photographs a subject's eye in a photographing mode selected by the photographing mode selection processor, a vision fixation optical system including a vision fixation target display that displays a vision fixation target, the vision fixation optical system projecting an image of the vision fixation target displayed in the vision fixation target display on the subject's eye, and a control processor that changes an amount of light of the vision fixation target in accordance with the photographing mode selected by the photographing mode selection processor.

8 Claims, 11 Drawing Sheets

(56) References Cited

U.S. PATENT DOCUMENTS

2015/0085252 A1 3/2015 Fujimura et al.
2015/0208243 A1* 7/2015 Dossas ................ H04W 12/08
455/410

* cited by examiner

FIG.5

| PHOTOGRAPHING MODE | AMOUNT OF LIGHT |
|---|---|
| COLOR PHOTOGRAPHING MODE | Q1 |
| FLUORESCENT PHOTOGRAPHING MODE | Q2 |

FIG.9

| PHOTOGRAPHING MODE | AMOUNT OF LIGHT | COLOR | LIGHTING PATTERN |
|---|---|---|---|
| COLOR PHOTOGRAPHING MODE | Q1 | GREEN | LIGHTING |
| FLUORESCENT PHOTOGRAPHING MODE | Q2 | BLUE | BLINKING |

OPHTHALMOLOGICAL APPARATUS

BACKGROUND OF THE INVENTION

Field of the Invention

The present invention relates to an ophthalmological apparatus that optically inspects a subject's eye.

Description of the Related Art

The ophthalmological apparatus includes an ophthalmological imaging device for acquiring an image of a subject's eye, and an ophthalmological measuring device for measuring characteristics of the subject's eye.

Examples of the ophthalmological imaging device are as follows: an optical coherence tomograph that acquires a tomographic image by using optical coherence tomography (OCT); a fundus camera for photographing a fundus; a scanning laser ophthalmoscope (SLO) that acquires an image of a fundus by using laser scanning with a confocal optical system; a slit lamp that acquires an image by using slit light to cut off an optical section of a cornea; and the like.

In addition, examples of the ophthalmological measuring device are as follows: an inspection device for refraction of eye (a refraction meter, or a keratometer) that measures refraction characteristics of a subject's eye; a tonometer; a specular microscope that acquires characteristics of a cornea (such as cornea thickness, and cell distribution); a wavefront analyzer that acquires aberration information on a subject's eye by using a Hartmann-Shack sensor; and the like.

There is known a conventional ophthalmological apparatus that has a plurality of photographing modes, such as a color photographing mode, and a fluorescent photographing mode, to perform photographing suitable for a purpose of inspection (refer to Japanese Patent Application Laid-Open No. 2008-289579, for example). In this kind of ophthalmological apparatus, setting of various optical systems (such as an illumination optical system, and a photographic optical system) is generally changed in accordance with a photographing mode selected.

In the ophthalmological apparatus, a vision fixation target is projected on a subject's eye before photographing for vision fixation of the subject's eye. The term, "vision fixation", means that the vision fixation target is projected toward the subject's eye to keep a line of sight direction of the subject's eye constant. In photographing of a fundus, a "vision fixation direction (vision fixation position)" can be considered as a "photographing portion (portion of interest)" on a premise that vision fixation is reliably performed. The term, "portion of interest", means a portion on which an inspector focuses during observation, such as an optic disk, and a macula lutea, in ophthalmology.

SUMMARY OF THE INVENTION

Unfortunately, there is a problem in which, since an amount of light of a vision fixation target projected on a subject's eye is always constant in the conventional ophthalmological apparatus, vision fixation in accordance with a photographing mode cannot be stable.

For example, if color photographing is performed in a non-mydriasis state, fundus photographing of a subject's eye in a dark place is performed in a natural mydriasis state. As a result, a too-bright vision fixation target projected on the subject's eye causes miosis, so that the photographing fails to be performed in a desirable state. Thus, it is desirable that the vision fixation target is set dark.

Meanwhile, in fluorescent photographing, continuous photographing is performed multiple times (a few times to a few dozen times) during a short time (a few seconds to a few dozen seconds) to photograph a process in which a fluorescent agent spreads in a blood vessel at a fundus. Thus, during the fluorescent photographing, persistence of vision caused by flash tends to remain. As a result, if a vision fixation target projected on a subject's eye is set dark, visibility of the vision fixation target deteriorates.

The present invention is made in light of the above-mentioned circumstances, and it is an object to provide an ophthalmological apparatus capable of optimizing vision fixation in accordance with a photographing mode.

In order to achieve the object described above, an ophthalmological apparatus in accordance with a first aspect of the present invention includes: a photographing mode selection processor that selects any one of a plurality of photographing modes including a color photographing mode and a fluorescent photographing mode; a photographic optical system that photographs a subject's eye in a photographing mode selected by the photographing mode selection processor; a vision fixation optical system including a vision fixation target display that displays a vision fixation target, the vision fixation optical system projecting an image of the vision fixation target displayed in the vision fixation target display on the subject's eye; and a control processor that changes an amount of light of the vision fixation target in accordance with the photographing mode selected by the photographing mode selection processor.

In the first aspect, an ophthalmological apparatus in accordance with a second aspect of the present invention allows the control processor to increase the amount of light of the vision fixation target in a case where the fluorescent photographing mode is selected as compared with a case where the color photographing mode is selected.

In the first aspect or the second aspect, an ophthalmological apparatus in accordance with a third aspect of the present invention allows the control processor to change a color of the vision fixation target in accordance with the photographing mode selected by the photographing mode selection processor.

In any of the first to third aspects, an ophthalmological apparatus in accordance with a fourth aspect of the present invention allows the control processor to allow the vision fixation target to light or blink in accordance with the photographing mode selected by the photographing mode selection processor.

In any of the first to fourth aspects, an ophthalmological apparatus in accordance with a fifth aspect of the present invention further includes a detector that detects whether there is miosis of the subject's eye on the basis of an image photographed by the photographic optical system, and allows the control processor to reduce the amount of light of the vision fixation target if the detector detects miosis of the subject's eye.

The present invention enables vision fixation to be optimized in accordance with a photographing mode.

BRIEF DESCRIPTION OF THE DRAWINGS

FIG. 5 is a table showing a correspondence between the photographing mode and the amount of light of the vision fixation target;

FIG. 9 is a table showing a correspondence between the photographing mode and the amount of light of the vision fixation target, a color, and a lighting pattern;

DETAILED DESCRIPTION OF THE PREFERRED EMBODIMENTS

An example of an ophthalmological apparatus in accordance with an embodiment of the present invention will be described in detail with reference to the accompanying drawings. The ophthalmological apparatus in accordance with the present invention is used for an optical inspection of a subject's eye. This kind of ophthalmological apparatus includes an ophthalmological imaging device, and an ophthalmological measuring device, as described before. The ophthalmological imaging device includes such as an optical coherence tomograph, a fundus camera, a scanning laser ophthalmoscope, and a slit lamp. The ophthalmological measuring device includes such as an inspection device for refraction of eye, a tonometer, a specular microscope, and a wavefront analyzer. Although the embodiments below describe in detail in a case where the present invention is applied to an optical coherence tomograph, the present invention is applicable to any another ophthalmological apparatus.

In the present specification, an image acquired by the OCT may be collectively called an OCT image. In addition, measurement operation to form an OCT image may be called OCT measurement. Contents of a description of a document described in the present specification may be appropriately applied as contents of the embodiment below.

Although the embodiment below describes an optical coherence tomograph that is provided with a low coherence light source and a spectroscope, and that uses an OCT of so-called a spectral domain type, the present invention is applicable to an optical coherence tomograph using an OCT method of a type other than the spectral domain type, such as a swept source type, and an en-face type. The swept source OCT is a method of sweeping wavelengths of light emitted to an object to be measured (wavelength sweep) to detect an interfering light acquired by superimposing a reflected light each of lights with the respective wavelengths and a reference light to acquire spectra intensity distribution, and then in the method, Fourier transform is applied to the spectra intensity distribution to image a form of the object to be measured. The en-face OCT is a method of emitting light with a predetermined beam diameter to an object to be measured to analyze components of an interfering light acquired by superimposing a reflected light of the emitted light and a reference light to form an image of the object to be measured in a cross section orthogonal to a direction of travel of the light, and the method is also called a full-field type.

Although the embodiment below describes an apparatus that is a combination of an OCT device and a fundus camera, an application item of the present invention is not limited to this kind of complex machine, the present invention is also applicable to an ophthalmological apparatus as a single machine (such as a fundus camera alone).

Configuration

Figure 1:
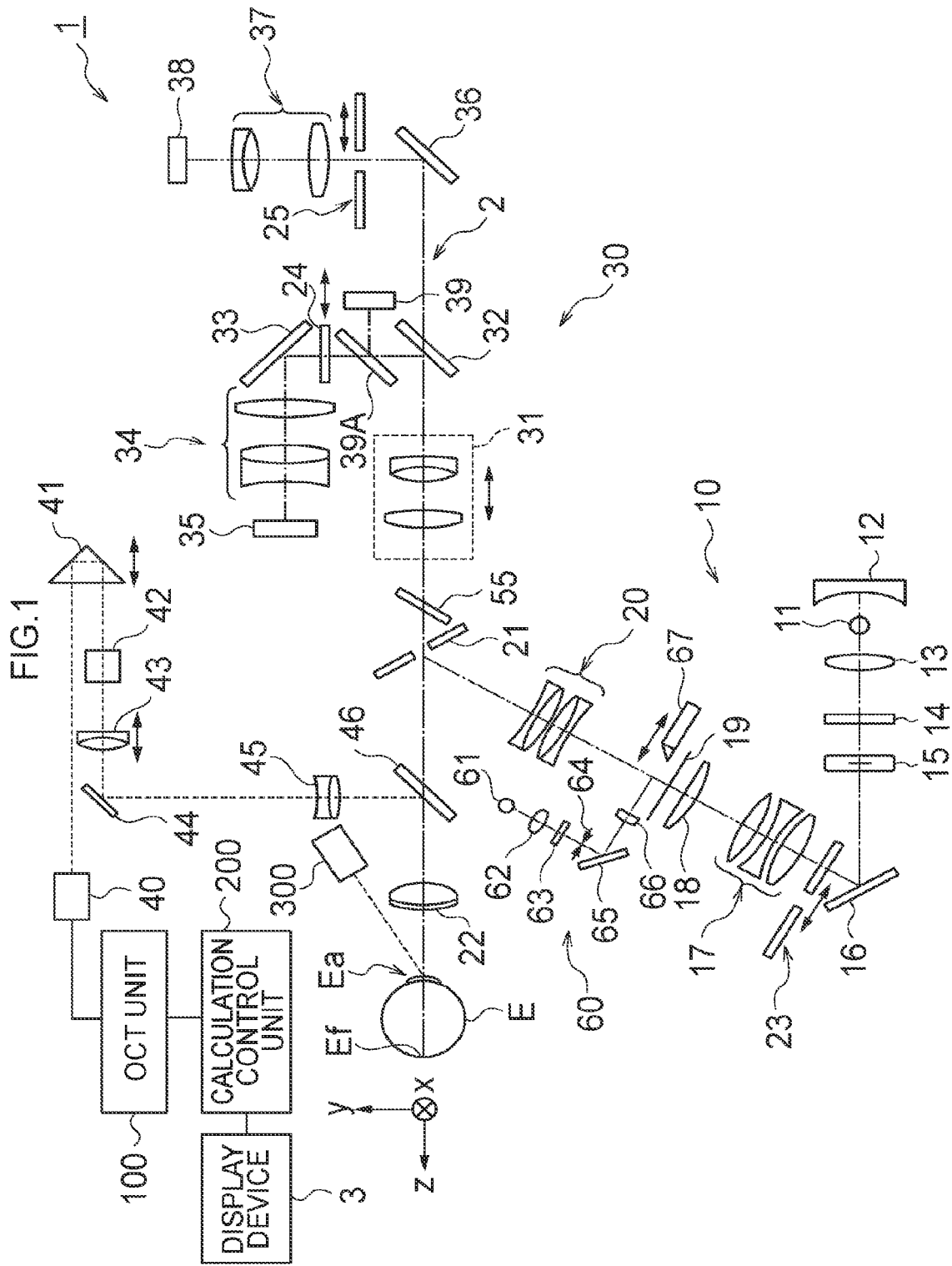
FIG. 1 is a schematic view showing an example of an entire configuration of an embodiment of an ophthalmological apparatus in accordance with the present invention.

As shown in FIG. 1, an ophthalmological apparatus 1 includes a fundus camera unit 2, an OCT unit 100, and a calculation control unit 200. The fundus camera unit 2 has an optical system that is almost the same as that of a conventional fundus camera. The OCT unit 100 is provided with an optical system for acquiring an OCT image of a fundus. The calculation control unit 200 includes a computer that performs various calculation processes, control processes, and the like.

Fundus Camera Unit

The fundus camera unit 2 shown in FIG. 1 is provided with an optical system for acquiring a two-dimensional image (fundus image) showing a surface form of a fundus Ef of a subject's eye E. The fundus image includes images such as an observation image and a photographed image. The observation image is a dynamic image of the fundus Ef photographed by using near infrared light, for example. The photographed image is a still image of the fundus Ef photographed by using a flash, for example. The still image includes a color image, a fluorescein fluorescent image, an indocyanine green fluorescent image, a spontaneous emission fluorescent image, and the like. The fundus camera unit 2 is also capable of photographing an anterior eye Ea of the subject's eye E.

Figure 4A:
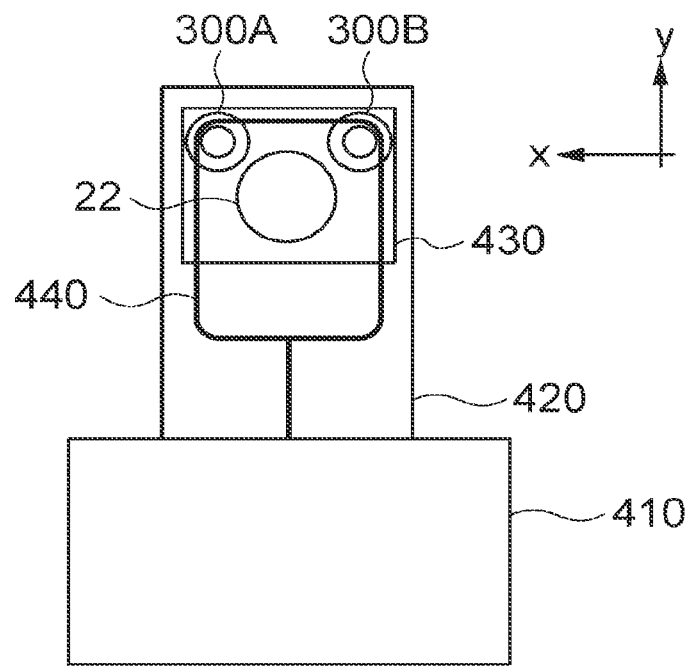
FIG. 4A is a schematic view showing an example of an appearance configuration of the embodiment of the ophthalmological apparatus in accordance with the present invention.
Figure 4B:
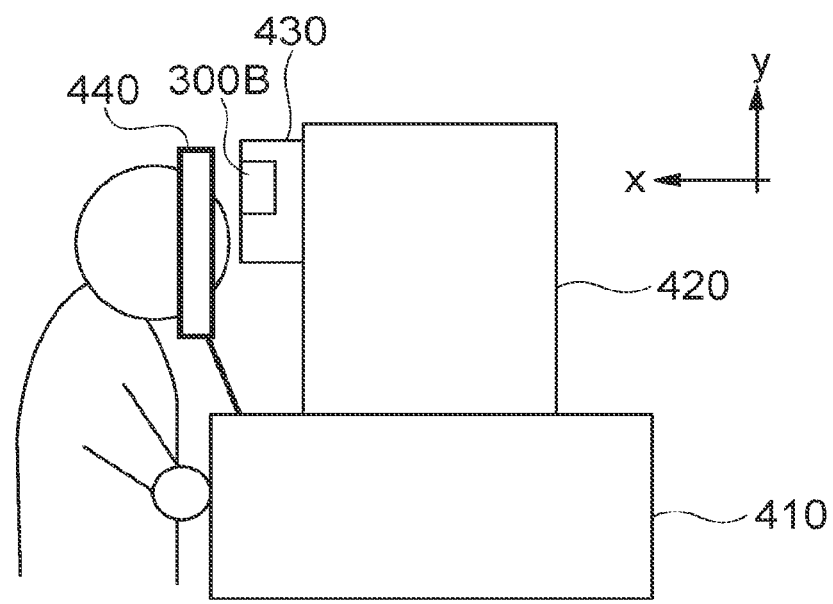
FIG. 4B is a schematic view showing an example of an appearance configuration of the embodiment of the ophthalmological apparatus in accordance with the present invention.

The fundus camera unit 2 is provided with a chin mount and a forehead pad to support a face of a subject. The chin mount and the forehead pad correspond to a support part 440 shown in FIGS. 4A and 4B. In FIGS. 4A and 4B, reference numerals 410, 420, and 430, designate: a base that stores a driving system, such as an optical system driving unit 2A and a calculation control circuit; a body provided on the base 410 to store an optical system; and a lens accommodation unit that is provided so as to project from a front face of the body 420 to store an objective lens 22, respectively.

The fundus camera unit 2 is provided with an illumination optical system 10 and a photographic optical system 30. The illumination optical system 10 emits illumination light to the fundus Ef. The photographic optical system 30 guides light reflected by the fundus in the illumination light to imaging devices (CCD image sensors 35 and 38, or may be simply called CCDs). The photographic optical system 30 guides signal light from the OCT unit 100 to the fundus Ef as well as the signal light passing through the fundus Ef to the OCT unit 100.

An observation light source 11 of the illumination optical system 10 is composed of a halogen lamp, for example. Light outputted from the observation light source 11 (observation illumination light) is reflected by a reflection mirror 12 with a curved reflection surface to pass through a visible light cut filter 14 via a condenser lens 13 to become near infrared light. In addition, the observation illumination light temporarily converges at a portion near a photographing light source 15 to be reflected by a mirror 16 to pass through relay lenses 17 and 18, a diaphragm 19, and a relay lens 20. Then the observation illumination light is reflected by a peripheral portion in a mirror with an aperture 21 (an area of a periphery of the aperture) to pass through a dichroic mirror 46 to be refracted by the objective lens 22 to illuminate the fundus Ef. For the observation light source, a light emitting diode (LED) is also available. An optical filter unit 23 will be described later.

Light reflected by the fundus in the observation illumination light is refracted by the objective lens 22 to pass through the dichroic mirror 46 to pass through an aperture formed in a center area of the mirror with an aperture 21, and then passes through a dichroic mirror 55 to be reflected by a dichroic mirror 32 via a focal lens 31. In addition, the light reflected by the fundus passes through a half mirror 39A to be reflected by a dichroic mirror 33, and then is imaged in a receiving surface of a CCD image sensor 35 through a condenser lens 34. The CCD image sensor 35 detects the light reflected by the fundus at a predetermined frame rate, for example. A display device 3 displays an image (observation image) based on the light reflected by the fundus detected by the CCD image sensor 35. A display device 3 displays an image (observation image) based on the light reflected by the fundus detected by the CCD image sensor 35. If the photographic optical system is focused on the anterior eye, an observation image of the anterior eye of the subject's eye E is displayed. An optical filter unit 24 will be described later.

The photographing light source 15 is composed of a xenon lamp, for example. Light outputted from the photographing light source 15 (photographing illumination light) passes through a path, as with observation illumination light, to be emitted to the fundus Ef. The light reflected by the fundus in the photographing illumination light passes through a path, as with the observation illumination light, to be guided to the dichroic mirror 32 to pass through the dichroic mirror 32, and then is reflected by a mirror 36 to be imaged in a receiving surface of a CCD image sensor 38 through a condenser lens 37. The display device 3 displays an image (photographed image) based on the light reflected by the fundus detected by the CCD image sensor 38. The display devices 3 for displaying the observation image and the photographed image may be the same or different. In a case where the subject's eye E is illuminated with infrared light to perform similar photographing, an infrared photographed image is displayed. An LED is also available for the photographing light source. The optical filter units 23, 24, and 25 will be described.

Each of the optical filter units 23, 24, and 25 includes an optical filter for various applications. The optical filter includes a filter for fluorescent photographing, a filter for red-free photographing, and the like. The optical filter for fluorescent photographing includes filters, such as for spontaneous emission fluorescent photographing (FAF), fluorescein fluorescent photographing (FA), indocyanine green photographing (ICG), and the like. The optical filter is not limited to these filters, and thus any optical filter used in various photographing methods in the ophthalmology field is available.

As a specific example, a filter for fluorescent photographing will be described. The optical filter unit 23 is provided with an exciter filter for FAF, an exciter filter for FA, and an exciter filter for ICG. Each of the exciter filters is detachable to an optical path of the illumination optical system 10. The optical filter unit 24 is provided with a barrier filter for FAF. The barrier filter is detachable to an optical path connecting the dichroic mirror 32 and the CCD image sensor 35. The optical filter unit 25 is provided with a barrier filter for FA, and a barrier filter for ICG. Each of the barrier filters is detachable to an optical path connecting the dichroic mirror 32 and the CCD image sensor 38.

A liquid crystal display (LCD) 39 displays a vision fixation target and an index of eyesight measurement. The vision fixation target is an index for vision fixation of the subject's eye E to be used at the time of fundus photographing, OCT measurement, or the like.

A part of light outputted from the LCD 39 is reflected by the half mirror 39A to be reflected by the dichroic mirror 32, and then passes through the aperture of the mirror with an aperture 21 via the focal lens 31 and the dichroic mirror 55 to pass through the dichroic mirror 46, and subsequently is refracted by the objective lens 22 to be projected on the fundus Ef.

Changing a display position of the vision fixation target in a screen of the LCD 39 enables a projection direction of the vision fixation target with respect to the subject's eye E, or a vision fixation position of the subject's eye E, to be changed. For example, as with a conventional fundus camera, the vision fixation position of the subject's eye E includes positions, such as: a position for acquiring an image in which a macula lutea of the fundus Ef is centered; a position for acquiring an image in which an optic disk is centered; and a position for acquiring an image in which the center of the fundus, positioned between the macula lutea and the optic disk, is centered. In addition, it is also possible to arbitrarily change the display position of the vision fixation target. A configuration for vision fixation of the subject's eye E corresponds to an example of "Vision Fixation Optical System". In addition, the LCD 39 that displays the vision fixation target corresponds to an example of the "vision fixation target display".

The amount of light of the vision fixation target (brightness) displayed in a screen of the LCD 39 is changed in accordance with each of photographing modes described later. The photographing modes include a color photographing mode, a fluorescent photographing mode (such as the spontaneous emission fluorescent photographing, the fluorescein fluorescent photographing, and the indocyanine green photographing), and the like. The amount of light of the vision fixation target is controlled by the control unit 210 described later.

Means for projecting a vision fixation target on the subject's eye E is not limited to the above. For example, providing a LED group composed of an array of a plurality of LEDs to allow the LEDs to selectively light enables a vision fixation position to be changed. In addition, providing one or more movable LEDs also enables a vision fixation position to be changed.

The fundus camera unit 2 includes a focus optical system 60. The focus optical system 60 creates an index (split index) for focusing on the fundus Ef.

When focus adjustment is performed, a reflection surface of a reflection bar 67 is provided at an angle in an optical path of the illumination optical system 10. Light (focus light) outputted from a LED 61 of the focus optical system 60 passes through a relay lens 62 to be split into two pencils of light by a split index plate 63 to pass through a two-aperture diaphragm 64, and then is reflected by a mirror 65 to be temporarily imaged on the reflection surface of the reflection bar 67 through a condenser lens 66 to be reflected. Then, the focus light is reflected by the mirror with an aperture 21 via the relay lens 20 to pass through the dichroic mirror 46, and then is refracted by the objective lens 22 to be projected on the fundus Ef.

Light reflected by the fundus in the focus light passes through a path, as with light reflected a cornea in alignment light, to be detected by the CCD image sensor 35. A light-receiving image (split index) created by the CCD image sensor 35 is displayed in the display device 3 together with the observation image. The calculation control unit 200, as before, analyzes a position of the split index to allow the focal lens 31 and the focus optical system 60 to move for focusing (autofocus function). The focusing may be manually performed while the split index is visually identified.

The dichroic mirror 46 allows an optical path for OCT measurement to branch from an optical path for fundus photographing. The dichroic mirror 46 reflects light within a wavelength range to be used for the OCT measurement, and allows light for fundus photographing to pass therethrough. The optical path for OCT measurement includes a collimator lens unit 40, an optical path length change unit 41, a galvanoscanner 42, a focal lens 43, a mirror 44, and a relay lens 45, in order from an OCT unit 100 side.

The optical path length change unit 41 is movable in a direction of an arrow shown in FIG. 1 to change length of the optical path for OCT measurement. This change in length of the optical path is used for correction of length of the optical path in accordance with eye axial length of the subject's eye E, adjustment of conditions of interference, and the like. The optical path length change unit 41 includes, for example, a corner cube, and a mechanism for moving the corner cube.

The galvanoscanner 42 changes a direction of travel of light (signal light LS) passing through the optical path for OCT measurement. Accordingly, it is possible to scan the fundus Ef with the signal light LS. The galvanoscanner 42 includes, for example, a galvanomirror that allows the signal light LS to sweep in an x-direction, a galvanomirror that allows the signal light LS to sweep in a y-direction, and a mechanism for independently driving the galvanomirrors. Accordingly, it is possible to allow the signal light LS to sweep in any direction in an xy-plane.

The fundus camera unit 2 includes an anterior eye camera 300. The anterior eye camera 300 substantially simultaneously photographs the anterior eye Ea from different directions. In this embodiment, the fundus camera unit 2 is provided in its face on a subject side with two cameras (refer to anterior eye cameras 300A and 300B shown in FIG. 4A). Each of the anterior eye cameras 300A and 300B, as shown in FIGS. 1 and 4A, is provided at a position away from the optical path of the illumination optical system 10 and an optical path of the photographic optical system 30. Hereinafter, the two anterior eye cameras 300A and 300B may be collectively designated by a reference numeral 300.

Although the two anterior eye cameras 300A and 300B are provided in this embodiment, the number of anterior eye cameras in the present invention is an arbitrary number of two or more. However, in consideration of calculation processing described later, even configuration capable of substantially simultaneously photographing an anterior eye from two different directions is available. In addition, in this embodiment, although the illumination optical system 10 and the photographic optical system 30 are individually provided with the anterior eye camera 300, at least the photographic optical system 30 enables similar anterior eye photographing to be performed. Thus, a configuration in which one of two or more anterior eye cameras is provided in the photographic optical system 30 may be available. That is, this embodiment allows any configuration capable of substantially simultaneously photographing an anterior eye from two (or more) different directions.

The term, "substantially simultaneously", shows that a deviation of photographing timing that is negligible compared with eye movement is allowed in photographing with two or more anterior eye cameras. Accordingly, it is possible to acquire images at the time when the subject's eye E is at substantially the same position (direction) with two or more anterior eye cameras.

Although the photographing with two or more anterior eye cameras is available for taking a moving image and a still image, this embodiment will particularly describe a case of taking a moving image in detail. In a case of taking a moving image, control of matching timing of starting taking the image, and of a frame rate and timing of taking an image at each frame, enables photographing of an anterior eye of the "substantially simultaneously" described above to be achieved. Meanwhile, in a case of taking a still image, control of matching timing of starting taking the image enables the photographing of an anterior eye described above.

This embodiment, as described in detail later, enables positioning (alignment) of an optical system for inspection with respect to the subject's eye E to be performed by using two anterior eye cameras 300A and 300B.

OCT Unit

Figure 2:
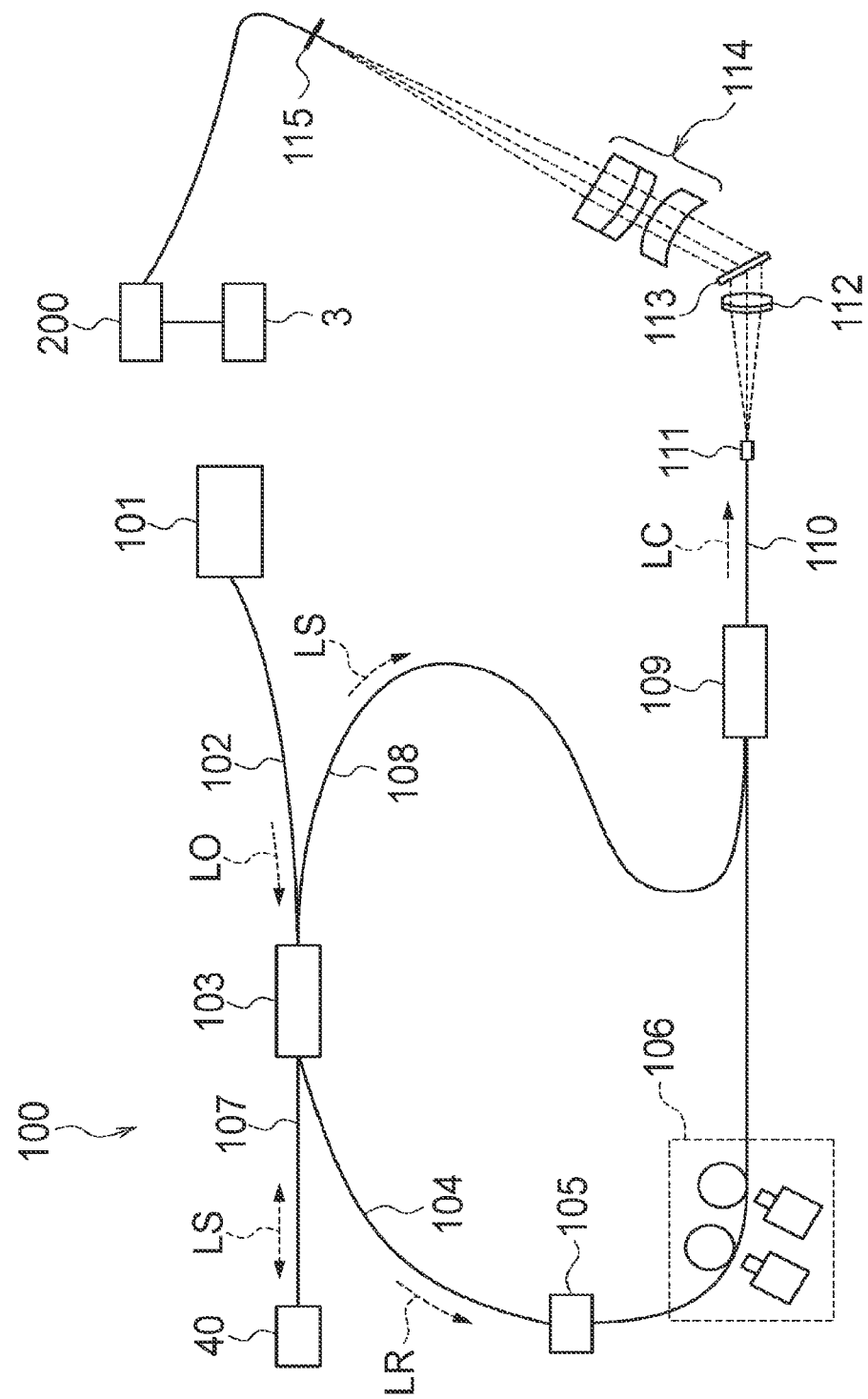
FIG. 2 is a schematic view showing an example of a configuration of an OCT unit in the embodiment of the ophthalmological apparatus in accordance with the present invention.

With reference to FIG. 2, an example of a configuration of the OCT unit 100 will be described. The OCT unit 100 is provided with an optical system for acquiring an OCT image of the fundus Ef. The optical system has a similar configuration to that of an OCT device of a conventional spectral domain type. That is, the optical system is configured to split low coherence light into reference light and signal light, and allows the signal light via the fundus Ef and the reference light via a reference optical path to interfere with each other to create interfering light so as to detect spectra components of the interfering light. This detection result (detection signal) is transmitted to the calculation control unit 200.

An OCT device of a swept source type includes a wavelength swept light source instead of a light source for outputting low coherence light, but does not include an optical member for applying spectral resolution to interfering light. Generally, a well-known art corresponding to a type of an OCT is arbitrarily applicable to a configuration of the OCT unit 100.

The light source unit 101 outputs wide-band low coherence light L0. The low coherence light L0 has, for example, a wavelength range in a near infrared region (of the order of 800 nm to 900 nm), and temporal coherence length of the order of a few tens micro meters. A wavelength range invisible to a human eye, such as near infrared light having a central wavelength of the order of 1040 nm to 1060 nm, may be available for the low coherence light L0.

The light source unit 101 includes an optical output device, such as a super luminescent diode (SLD), an LED, and a semiconductor optical amplifier (SOA).

The low coherence light L0 outputted from the light source unit 101 is guided to a fiber coupler 103 through an optical fiber 102 to be split into the signal light LS and reference light LR.

The reference light LR is guided through the optical fiber 104 to reach an optical attenuator 105. The optical attenuator 105 automatically adjusts an amount of reference light LR to be guided into the optical fiber 104 by using a well-known art under control of the calculation control unit 200. The reference light LR, whose amount is adjusted by the optical attenuator 105, is guided through the optical fiber 104 to reach a polarization regulator (polarization controller) 106. The polarization regulator 106 applies stress to the optical fiber 104 formed into the shape of a loop from the outside, for example, to adjust a polarization state of the reference light LR guided through the optical fiber 104. The polarization regulator 106 is not limited to this configuration, and thus any well-known art is available. The reference light LR, whose polarization state is adjusted by the polarization regulator 106, reaches a fiber coupler 109.

The signal light LS created by the fiber coupler 103 is guided through the optical fiber 107 to be formed into a parallel pencil by the collimator lens unit 40. In addition, the signal light LS reaches the dichroic mirror 46 via the optical path length change unit 41, the galvanoscanner 42, the focal lens 43, the mirror 44, and the relay lens 45. Then the signal light LS is reflected by the dichroic mirror 46 to be refracted by the objective lens 22 to illuminate the fundus Ef. The signal light LS is scattered (including reflection) in various depth positions of the fundus Ef. Backscattered light of the signal light LS scattered by the fundus Ef inversely travels through the same path as that of incidence to be guided through the fiber coupler 103 to reach the fiber coupler 109 via the optical fiber 108.

The fiber coupler 109 allows the backscattered light of the signal light LS and the reference light LR via the optical fiber 104 to interfere with each other. The interfering light LC created in this way is guided through the optical fiber 110 to be emitted from an emission end 111. In addition, the interfering light LC is formed into a parallel pencil through a collimator lens 112 to be dispersed (spectral resolution) through a diffraction grating 113, and then is concentrated through a condenser lens 114 to be projected on a receiving surface of a CCD image sensor 115. Although the diffraction grating 113 shown in FIG. 2 is a transmission type, a spectroscopic element of another type, such as a diffraction grating of a reflection type, is also available.

The CCD image sensor 115 is, for example, a line sensor that detects each spectra component of the interfering light LC dispersed, and converts it into electric charge. The CCD image sensor 115 accumulates the electric charge to create a detection signal, and then transmits the signal to the calculation control unit 200.

Although this embodiment uses a Michelson type interferometer, any type of interferometer, such as a Mach-Zehnder type, may be appropriately used. Instead of the CCD image sensor, an image sensor of another type, such as a complementary metal oxide semiconductor (CMOS) image sensor, is available.

Calculation Control Unit

A configuration of the calculation control unit 200 will be described. The calculation control unit 200 analyzes a detection signal received from the CCD image sensor 115 to create an OCT image of the fundus Ef. Calculation processing for that is the same as that of an OCT device of a conventional spectral domain type.

The calculation control unit 200 controls each of the fundus camera unit 2, the display device 3, and the OCT unit 100. For example, the calculation control unit 200 allows the display device 3 to display an OCT image of the fundus Ef.

In addition, the calculation control unit 200 performs control of the fundus camera unit 2, such as: control of operation of the observation light source 11, the photographing light source 15, and the LED 61; control of operation of the LCD 39; control of movement of the focal lenses 31 and 43; control of movement of the reflection bar 67; control of movement of the focus optical system 60; control of movement of the optical path length change unit 41; control of operation of the galvanoscanner 42; and control of operation of the anterior eye camera 300.

Further, the calculation control unit 200 performs control of the OCT unit 100, such as: control of operation of the light source unit 101; control of operation of the optical attenuator 105; control of operation of the polarization regulator 106; and control of operation of the CCD image sensor 115.

The calculation control unit 200, for example, as with a conventional computer, includes a microprocessor, a RAM, a ROM, a hard drive, a communication interface, and the like. A storage device, such as the hard drive, stores a computer program for controlling the ophthalmological apparatus 1. The calculation control unit 200 may include various circuit boards, such as that for forming an OCT image. In addition, the calculation control unit 200 may include an operation device (input device), such as a keyboard and a mouse, and a display device, such as a LCD.

The fundus camera unit 2, the display device 3, the OCT unit 100, and the calculation control unit 200, may be integrally formed (or formed in a single body), or may be separately formed in two or more bodies.

Control System

Figure 3:
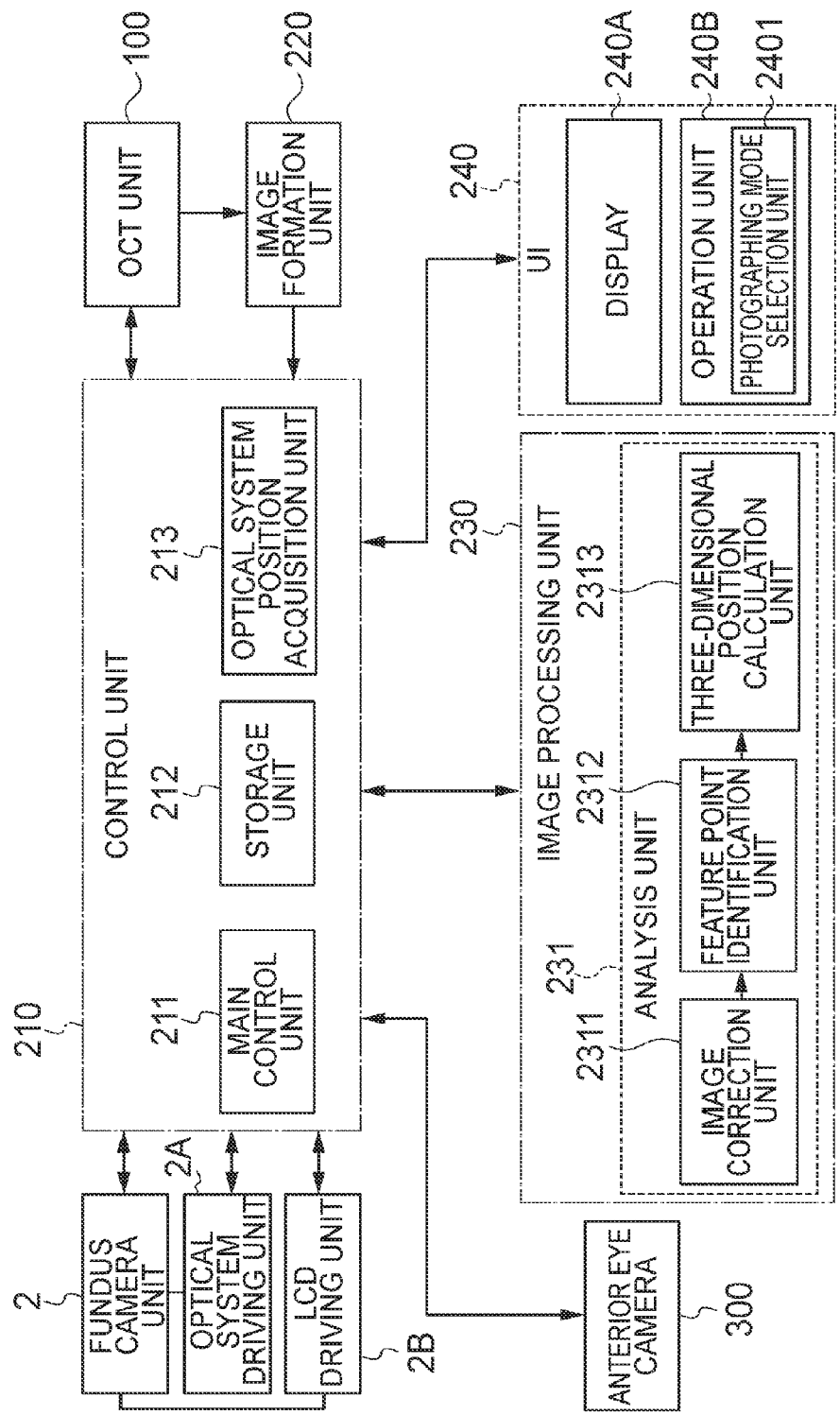
FIG. 3 is a schematic block diagram view showing an example of a configuration of a control system of the embodiment of the ophthalmological apparatus in accordance with the present invention.

A configuration of a control system of the ophthalmological apparatus 1 will be described with reference to FIG. 3.

Control Unit

The control system of the ophthalmological apparatus 1 is mainly composed of a control unit 210. The control unit 210, for example, includes the microprocessor, the RAM, the ROM, the hard drive, the communication interface, and the like, described before. The control unit 210 is provided with a main control unit 211, a storage unit 212, and an optical system position acquisition unit 213.

Main Control Unit

The main control unit 211 performs various control processes of operation described before. Control of movement of the focal lens 31 is performed by controlling a focal driving unit (not shown) to move the focal lens 31 in the direction of the optical axis. Accordingly, an in-focus position of the photographic optical system 30 is changed. In addition, the main control unit 211 is capable of controlling the optical system driving unit 2A to move an optical system provided in the fundus camera unit 2 in a three-dimensional manner.

Although the optical system driving unit 2A of this embodiment moves the optical system provided in the fundus camera unit 2, the optical system driving unit 2A may be configured so as to move the optical system provided in the fundus camera unit 2 as well as an optical system provided in the OCT unit 100.

Since the anterior eye camera 300 of this embodiment is provided in a body of the fundus camera unit 2, controlling the optical system driving unit 2A enables the anterior eye camera 300 to be moved. It is also possible to provide a photographing moving unit capable of independently moving each of two or more anterior eye cameras 300. Specifically, the photographing moving unit may include a drive mechanism (such as an actuator, and a power transmission mechanism) provided in each of the anterior eye cameras 300. In addition, the photographing moving unit may be configured so as to transmit power generated by a single actuator to a power transmission mechanism provided for each of the anterior eye cameras 300 to move the two or more anterior eye cameras 300.

In addition, the main control unit 211 is capable of controlling an LCD driving unit 2B to change the amount of light of the vision fixation target displayed in the LCD 39 (refer to FIG. 1) of the fundus camera unit 2 in accordance with a photographing mode set by a photographing mode selection unit 2401 described later. As described later, the main control unit 211 may also change a color or a lighting pattern (lighting/blinking) of the vision fixation target along with the amount of light of the vision fixation target.

The main control unit 211 performs processing of writing data into the storage unit 212, and processing of reading out data from the storage unit 212.

Storage Unit

The storage unit 212 stores various data items. The data stored in the storage unit 212 includes, for example, image data on an OCT image, image data on a fundus image, information on a subject's eye, and the like. The information on a subject's eye includes information on a subject, such as a patient ID and a name, and information on a subject's eye, such as information on identification of left eye/right eye. In addition, the storage unit 212 stores various programs and data items for operating the ophthalmological apparatus 1.

In addition, the storage unit 212 previously stores a table (LUT) shown in FIG. 5. FIG. 5 is the table showing a correspondence between the photographing mode and the amount of light of the vision fixation target. Accordingly, if a photographing mode is set by a photographing mode selection unit 2401 described later, the main control unit 211 is capable of controlling the amount of light of the vision fixation target displayed in the LCD 39 to be changed in accordance with the photographing mode set with reference to the table shown in FIG. 5. That is, the main control unit 211 sets the amount of light of the vision fixation target at Q1 if the color photographing mode is selected. Meanwhile, if the fluorescent photographing mode is selected, the amount of light of the vision fixation target is set at Q2 (Q2>Q1). That is, the main control unit 211 controls the amount of light of the vision fixation target to increase in a case where the fluorescent photographing mode is selected as compared with a case where the color photographing mode is selected.

The storage unit 212 previously stores information on aberration (not shown). The information on aberration includes information on distortion aberration that occurs in a photographed image due to influence of an optical system provided in each of the anterior eye cameras 300. The optical system provided in the anterior eye camera 300 includes, for example, optical elements, such as a lens that causes distortion aberration to occur. It can be said that the information on aberration is a parameter in which distortion given to a photographed image by these optical elements is quantified. A specific example of a method of creating the information on aberration is, for example, described in Japanese Patent Application Laid-Open No. 2013-248376 filed by the present applicant.

Optical System Position Acquisition Unit

The optical system position acquisition unit 213 acquires a current position of the optical system for inspection provided in the ophthalmological apparatus 1. The optical system for inspection is used to optically inspect the subject's eye E. The optical system for inspection in the ophthalmological apparatus 1 (a complex machine of a fundus camera and an OCT device) of this embodiment is used to acquire an image of a subject's eye, and thus includes the photographic optical system 30.

The optical system position acquisition unit 213, for example, receives information showing contents of control of movement of the optical system driving unit 2A by the main control unit 211 to acquire a current position of the optical system for inspection moved by the optical system driving unit 2A. A specific example of this processing will be described. The main control unit 211 controls the optical system driving unit 2A at predetermined timing (such as at the time of starting a device, and of inputting information on a patient) to move the optical system for inspection to a predetermined initial position. After then, the main control unit 211 records contents of control every time when the optical system driving unit 2A is controlled. Accordingly, it is possible to acquire history of contents of the control. The optical system position acquisition unit 213 acquires contents of the control up to the present with reference to the history to acquire a current position of the optical system for inspection on the basis of the contents of the control.

In addition, every time when the main control unit 211 controls the optical system driving unit 2A, contents of the control may be transmitted to the optical system position acquisition unit 213 so that the optical system position acquisition unit 213 sequentially acquires a current position of the optical system for inspection every time when receiving the contents of the control.

As another example of a configuration, a position sensor for detecting a position of the optical system for inspection may be provided in the optical system position acquisition unit 213.

In a case where the optical system position acquisition unit 213 acquires a current position of the optical system for inspection as above, the main control unit 211 is able to acquire information on positional displacement of the optical system for inspection with respect to the subject's eye E on the basis of the current position acquired and a three-dimensional position of the subject's eye E acquired by an analysis unit 231 described later. Specifically, the main control unit 211 identifies the current position of the optical system for inspection by using a result acquired by the optical system position acquisition unit 213, as well as the three-dimensional position of the subject's eye E by using a result analyzed by the analysis unit 231. Next, the main control unit 211 acquires an amount and direction of the positional displacement from a proper position of the optical system for inspection with respect to the subject's eye E in each of the x-direction (side-to-side direction), the y-direction (vertical direction), and the z-direction (direction of working distance), on the basis of the current position of the optical system for inspection, and the three-dimensional position identified by the analysis unit 231. Then, the main control unit 211 allows a pseudo alignment index image and an alignment reference position mark to be displayed at a predetermined position in a screen of a display 240A by superimposing them on an observation image to form a composite display in accordance with the amount of positional displacement in each of the directions and the direction of positional displacement acquired. The alignment reference position mark is an image showing a position to be a moving target of the pseudo alignment index image (such as an image of a parentheses-type), and is always displayed at a predetermined reference position regardless of change of a vision fixation position of the subject's eye E. The reference position means a central position of the observation image in the display 240A. An examiner operates an operation unit 240B to move the optical system for inspection in a three-dimensional manner so that the pseudo alignment index image displayed in a screen of the display 240A enters the alignment reference position mark to perform alignment of the optical system for inspection with respect to the subject's eye E.

Image Formation Unit

An image formation unit 220 forms image data on a tomographic image of the fundus Ef on the basis of a detection signal from the CCD image sensor 115. This processing includes noise elimination (noise reduction), filter processing, fast Fourier transform (FFT), and the like, as with the optical coherence tomography of a conventional spectral domain type. In a case of an OCT device of another type, the image formation unit 220 performs well-known processing corresponding to the type.

The image formation unit 220, for example, includes the circuit board described before. In the present specification, the "image data" and the "image" based on it may be identified.

Image Processing Unit

An image processing unit 230 applies various image processing items and analysis processing to an image formed by the image formation unit 220. For example, the image processing unit 230 performs various correction processing items, such as luminance correction of an image, and dispersion correction. In addition, the image processing unit 230 applies the various image processing items and the analysis processing to an image acquired by the fundus camera unit 2 (such as a fundus image, and an anterior eye image).

The image processing unit 230 performs well-known image processing, such as interpolation processing of interpolating pixels between tomographic images, to form image data on a three-dimensional image of the fundus Ef. The image data on a three-dimensional image means that a position of a pixel is defined by a three-dimensional coordinate system. The image data of a three-dimensional image includes image data composed of voxels arranged in a three-dimensional manner arrangement. The image data is called volume data, voxel data, or the like. In a case where an image based on volume data is displayed, the image processing unit 230 applies rendering processing (such as, volume rendering, and maximum intensity projection (MIP) or maximum value projection) to the volume data to form pseudo image data of a three-dimensional image as viewed from a specific line of sight direction. The display 240A displays the pseudo three-dimensional image.

It is also possible to form stack data on a plurality of tomographic images as image data of a three-dimensional image. The stack data is acquired by arranging a plurality of tomographic images acquired along a plurality of scanning lines in a three-dimensional manner on the basis of a positional relationship of the scanning lines. That is, the stack data is acquired by allowing a plurality of tomographic images defined by an originally individual two-dimensional coordinate system to be expressed by one three-dimensional coordinate system (or to be embedded in one three-dimensional space).

Analysis Unit

The image processing unit 230 is provided with the analysis unit 231. The analysis unit 231 analyzes two photographed images that are substantially simultaneously acquired by the anterior eye cameras 300A and 300B to acquire a three-dimensional position of the subject's eye E. As an example of a configuration to perform this processing, the analysis unit 231 includes an image correction unit 2311, a feature point identification unit 2312, and a three-dimensional position calculation unit 2313.

Image Correction Unit

The image correction unit 2311 corrects distortion of each of photographed images acquired by the anterior eye camera 300 on the basis of the aberration information stored in the storage unit 212. This processing, for example, is performed by using a well-known image processing art based on a correction coefficient for correcting distortion aberration. If distortion aberration of an optical system of the anterior eye camera 300 to be applied to a photographed image is sufficiently small, it is unnecessary to provide the aberration information and the image correction unit 2311, described above.

Feature Point Identification Unit

The feature point identification unit 2312 analyzes each of the photographed images, whose distortion aberration is corrected by the image correction unit 2311, to identify a position (referred to as a feature point position) in the photographed image corresponding to a predetermined feature point of the anterior eye Ea. For example, the center of a pupil or the tip of the cornea of the subject's eye E is applied to the predetermined feature point. Hereinafter, a specific example of processing of identifying the center of a pupil will be described.

First, the feature point identification unit 2312 identifies an image area (pupil area) corresponding to a pupil of the subject's eye E on the basis of distribution of pixel values (such as luminance values) of a photographed image. In general, since a pupil is imaged at brightness lower than other portions, searching for an image area with low brightness enables the pupil area to be identified. At this time, the pupil area may be identified in consideration of the shape of the pupil. That is, searching for an image area in a substantially circular shape as well as with low brightness enables the pupil area to be identified.

Next, the feature point identification unit 2312 identifies a center position of the pupil area identified. Since the pupil is in a substantially circular shape as described above, a contour of the pupil area is identified to allow a center position of an approximate ellipse of the contour to be identified to enable the center position to be set as the center of the pupil. In addition, the center of gravity of the pupil area may be acquired to be set as the center of a pupil.

Even if another feature point is applied, it is possible to identify a position of the feature point on the basis of distribution of pixel values of a photographed image, as described above.

Three-Dimensional Position Calculation Unit

The three-dimensional position calculation unit 2313 calculates a three-dimensional position of a feature point of the subject's eye E on the basis of a position of each of the two or more anterior eye cameras 300, and a position of the feature point in each of two or more photographed images identified by the feature point identification unit 2312. This processing will be described with reference to FIGS. 6A and 6B.

Figure 6A:
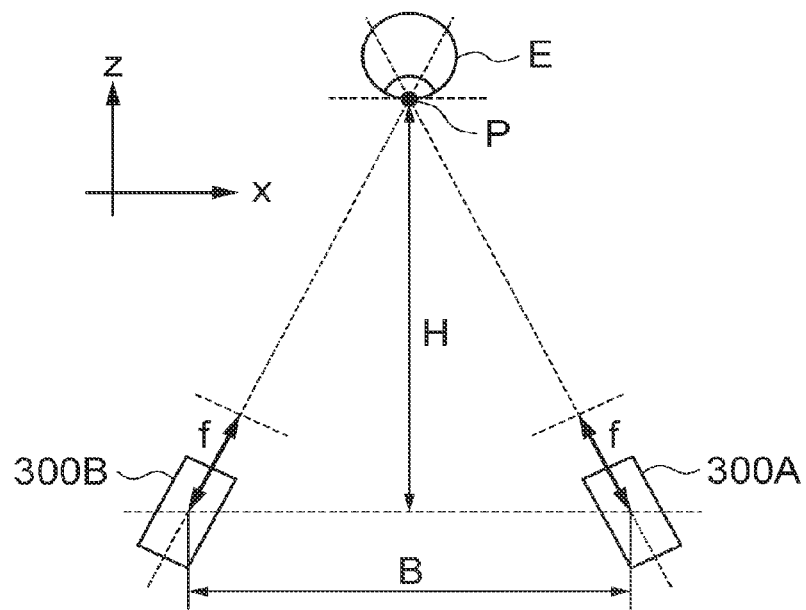
FIG. 6A is a schematic view to describe processing performed in the embodiment of the ophthalmological apparatus in accordance with the present invention.
Figure 6B:
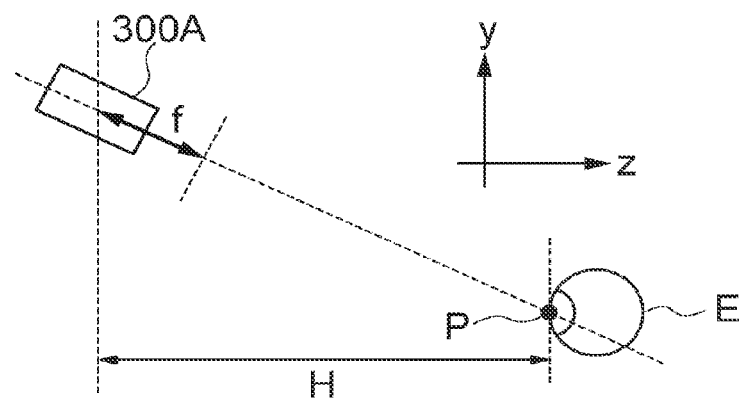
FIG. 6B is a schematic view to describe processing performed in the embodiment of the ophthalmological apparatus in accordance with the present invention.
Figure 7:
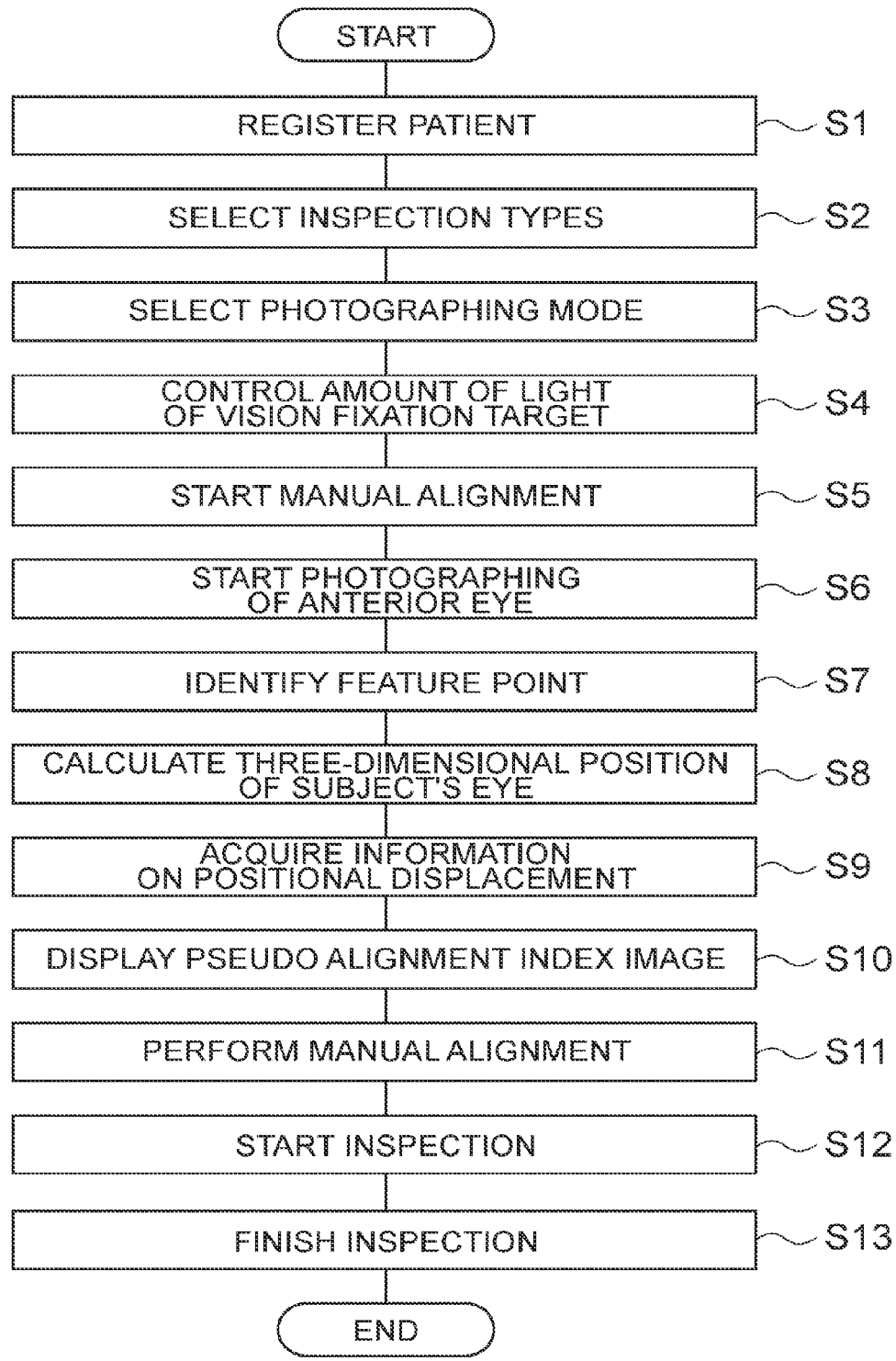
FIG. 7 is a flow chart showing an example of operation of the embodiment of the ophthalmological apparatus in accordance with the present invention.

FIG. 6A is a top view showing a positional relationship between the subject's eye E and the anterior eye cameras 300A and 300B. FIG. 6B is a side view showing a positional relationship between the subject's eye E and the anterior eye cameras 300A and 300B. A distance (baseline length) between the two anterior eye cameras 300A and 300B, a distance (photographing distance) between a baseline of the two anterior eye cameras 300A and 300B, and a feature point P of the subject's eye E, and a distance (screen distance) between each of the anterior eye cameras 300A and 300B, and its screen plane, are designated by "B", "H", and "f", respectively.

In this kind of arrangement, resolution of a photographed image acquired by the anterior eye cameras 300A and 300B is expressed by the following expressions.

Resolution in a $xy$-directions(plane resolution):
$\Delta xy = H \times \Delta p / f$ Resolution in the $z$-direction(depth resolution):
$\Delta z = H \times H \times \Delta p / (B \times f)$ where $\Delta p$ is pixel resolution.

The three-dimensional position calculation unit 2313 applies well-known trigonometry in consideration of the arrangement relationship shown in FIGS. 6A and 6B to a position of each of the anterior eye cameras 300A and 300B, which is known, and a position in each of two photographed images, corresponding to the feature point P, to calculate a three-dimensional position of the feature point P, or a three-dimensional position of the subject's eye E.

The three-dimensional position of the subject's eye E calculated by the three-dimensional position calculation unit 2313 is transmitted to the control unit 210.

In this embodiment, the anterior eye cameras 300A and 300B, and the analysis unit 231 are an example of the "subject's eye position acquisition unit". That is, in this embodiment, although the analysis unit 231 analyzes two photographed images that are substantially simultaneously acquired by the anterior eye cameras 300A and 300B to acquire a three-dimensional position of the subject's eye E, an aspect of acquiring the three-dimensional position of the subject's eye E is not limited to this embodiment. For example, the three-dimensional position of the subject's eye E may be acquired from a front face image of the subject's eye E (an observation image of the anterior eye Ea) by using an optical lever method, or may be acquired from an external device.

The image processing unit 230 serving as above includes, for example, the microprocessor, the RAM, the ROM, the hard drive, the circuit board, and the like, described before. A storage device, such as the hard drive, previously stores a computer program for allowing the microprocessor to perform the function described above.

User Interface

The user interface 240 includes the display 240A, and the operation unit 240B. The display 240A includes a display device of the calculation control unit 200 described before, and the display device 3. The operation unit 240B includes an operation device of the calculation control unit 200 described before. The operation unit 240B may include various buttons and keys, provided in a body of the ophthalmological apparatus 1 or in the outside. For example, if the fundus camera unit 2 has a body similar to that of a conventional fundus camera, the operation unit 240B may include a joystick, an operation panel, and the like, provided in the body. In addition, the display 240A may include various display devices, such as a touch panel provided in the body of the fundus camera unit 2.

The operation unit 240B includes the photographing mode selection unit 2401. The photographing mode selection unit 2401 includes buttons for setting a photographing mode, such as a color photographing mode selection button for selecting the color photographing mode, and a fluorescent photographing mode selection button for selecting the fluorescent photographing mode. The fluorescent photographing mode selection button is configured so as to enable a type of photographing, such as spontaneous emission fluorescent photographing, fluorescein fluorescent photographing, and indocyanine green fluorescent photographing, to be selected.

It is unnecessary that each of the display 240A and the operation unit 240B is configured as an individual device. For example, a device having a display function and an operation function, which are integrated, such as a touch panel, is also available. In that case, the operation unit 240B includes the touch panel, and a computer program. Operation contents with respect to the operation unit 240B are inputted into the control unit 210 as an electric signal. In addition, a graphical user interface (GUI) displayed in the display 240A and the operation unit 240B may be used for operation and information input.

Operation

Operation of the ophthalmological apparatus 1 will be described. A flow chart shown in FIGS. 6A and 6B shows an example of the operation of the ophthalmological apparatus 1.

S1: Patient Registration

First, the user inputs patient information on a subject by using the user interface 240. The patient information includes a patient ID, a patient name, and the like.

S2: Selection of Inspection Types

Subsequently, the user selects and inputs inspection types to be applied to the subject by using the user interface 240.

Items of the inspection types include: an inspection portion (such as a fundus central portion, a fundus peripheral portion, an optic disk, and a macula lutea); a subject's eye (such as a left eye, a right eye, both eyes); an image photographing pattern (such as only a fundus image, only an OCT image, and both the images); an OCT scan pattern (such as a line scan, a cross scan, a radial scan, a circular scan, and a three-dimensional scan); and the like. In this example of the operation, a peripheral portion in the fundus Ef is selected as an inspection portion.

S3: Selection of Photographing Mode

Next, the user selects a photographing mode by using the user interface 240. Specifically, the user selectively presses any one of a plurality of buttons for selecting a photographing mode, arranged in the photographing mode selection unit 2401, to select a photographing mode.

S4: Control of Amount of Light of Vision Fixation Target

Subsequently, the control unit 210 controls setting of each unit in accordance with the photographing mode selected by the photographing mode selection unit 2401. At the time, the control unit 210 changes a display position of a vision fixation target displayed in the LCD 39 according to an inspection portion, as well as controls the amount of light of the vision fixation target.

Specifically, the main control unit 211 controls the amount of light of the vision fixation target displayed in the LCD 39 to be changed in accordance with the photographing mode selected by the photographing mode selection unit 2401 with reference to a table (refer to FIG. 5) stored in the storage unit 212. That is, the main control unit 211 sets the amount of light of the vision fixation target at Q1 if the color photographing mode is selected. Meanwhile, if the fluorescent photographing mode is selected, the amount of light of the vision fixation target is set at Q2 (Q2>Q1). That is, the main control unit 211 controls the amount of light of the vision fixation target to increase in a case where the fluorescent photographing mode is selected as compared with a case where the color photographing mode is selected.

That is, if the amount of light of the vision fixation target displayed in the LCD 39 in a case where the color photographing mode is selected is set as a reference amount of light, the main control unit 211 controls the amount of light of the vision fixation target displayed in the LCD 39 to increase to more than the reference amount of light if the fluorescent photographing mode is selected.

The vision fixation target displayed in the LCD 39 as described above is projected on the subject's eye E. Then, vision fixation of the subject's eye E is performed on the basis of the vision fixation target.

S5: Start of Manual Alignment

Next, a start of manual alignment is instructed. The control unit 210 may automatically instruct the start after receiving the selection of a photographing mode shown in step S3, or the user may manually instruct the start by using the operation unit 240B.

S6: Start of Photographing of Anterior Eye

When the start of manual alignment is instructed, the control unit 210 allows each of the anterior eye cameras 300A and 300B to start photographing the anterior eye Ea. This photographing is of a moving image for the anterior eye Ea. Each of the anterior eye cameras 300A and 300B performs photographing of a moving image at a predetermined frame rate. Photographing timing of each of the anterior eye cameras 300A and 300B may be synchronized by the control unit 210. Each of the anterior eye cameras 300A and 300B sequentially transmits an acquired frame to the control unit 210 in real time. The control unit 210 allows frames acquired by both the anterior eye cameras 300A and 300B to be associated with each other in accordance with the photographing timing. That is, the control unit 210 allows frames that are substantially simultaneously acquired by both the anterior eye cameras 300A and 300B to be associated with each other. This association, for example, is made up on the basis of synchronization control as described above, or input timing of the frames from the anterior eye cameras 300A and 300B. The control unit 210 transmits a pair of frames associated with each other to the analysis unit 231.

S7: Identification of Feature Point

The image correction unit 2311 corrects distortion of each of the frames transmitted from the control unit 210 on the basis of aberration information stored in the storage unit 212. This correction processing is performed according to the manner described before. The pair of frames, in which distortion is corrected, is transmitted to the feature point identification unit 2312.

The feature point identification unit 2312 performs processing of analyzing each of the frames transmitted from the image correction unit 2311 to identify a position in each of the frames corresponding to a feature point (center of a pupil) of the anterior eye Ea.

If identification of the feature point fails, it is possible to control processing of identifying the feature point so as to be performed again after the anterior eye cameras 300A and 300B are moved in a direction away from the support part 440 and/or an outward direction from the support part 440. Moving the anterior eye cameras 300A and 300B in the direction away from the support part 440 increases a distance between the anterior eye cameras 300A and 300B, and the subject (subject's eye E) to enable a range wider than the subject's face to be photographed. Accordingly, a possibility that the subject's eye E may be arranged within a favorably photographable range by the anterior eye cameras 300A and 300B increases. In addition, moving the anterior eye cameras 300A and 300B in the outward direction from the support part 440 moves the anterior eye cameras 300A and 300B toward the subject's ear side to increase a possibility that the subject's eye E may be arranged within a favorably photographable range. Combination of movements in these two directions further increases a possibility that the subject's eye E may be arranged within a favorably photographable range.

It is also possible to determine whether an image corresponding to the anterior eye Ea is positioned within a prescribed area in a frame. If it is determined that the image of the anterior eye Ea is not positioned within the prescribed area, it is possible to perform control of movement of the anterior eye cameras 300A and 300B as with the description above.

S8: Calculation of Three-Dimensional Position of Subject's Eye

The three-dimensional position calculation unit 2313 calculates a three-dimensional position of a feature point (center of a pupil) of the subject's eye E on the basis of a position of each of the anterior eye cameras 300A and 300B, and a position of a feature point of each of the pair of frames identified by the feature point identification unit 2312. This processing is performed according to the manner described before.

S9: Acquisition of Information on Positional Displacement

The control unit 210 acquires information on positional displacement of the optical system for inspection with respect to the subject's eye E on the basis of the three-dimensional position of the feature point (center of a pupil) calculated in step S8. This processing, for example, is performed as follows. First, the control unit 210 acquires a current position of the optical system for inspection. The current position, for example, is acquired from control history with respect to the optical system driving unit 2A that moves the fundus camera unit 2. It is also possible to provide a position sensor that detects a position of the fundus camera unit 2 to acquire the current position from a detection result acquired by the position sensor. A coordinate system defining the three-dimensional position (coordinate) of the subject's eye E acquired in step S7 and a coordinate system defining current position (coordinate) of the optical system for inspection are to be common. Alternatively, coordinate transformation between both the coordinate systems is to be known.

The information on positional displacement shows displacement (an amount and direction of positional displacement) from a proper position of the optical system for inspection with respect to the subject's eye E. The proper position is a target position of favorable alignment of the optical system for inspection to the subject's eye E inspect. At the proper position, an axis of the subject's eye E and an optical axis of the optical system for inspection agree with each other in the x-direction (side-to-side direction) and the y-direction (vertical direction). The proper position is away from the subject's eye E in the z-direction (fore-and-aft direction, or optical axis direction) by a predetermined operation distance. Since the operation distance is known and the three-dimensional position of the subject's eye E is acquired in step S7, it is easy to acquire a coordinate of the target position of alignment in the common coordinate system.

S10: Display of Pseudo Alignment Index Image

The control unit 210 allows each of the pseudo alignment index image and the alignment reference position mark to be displayed at a predetermined position in a screen of the display 240A by superimposing them on an observation image to form a composite display on the basis of information on positional displacement acquired in step S9. A display example of the pseudo alignment index image and the alignment reference position mark will be described below.

Display Example

Figure 8A:
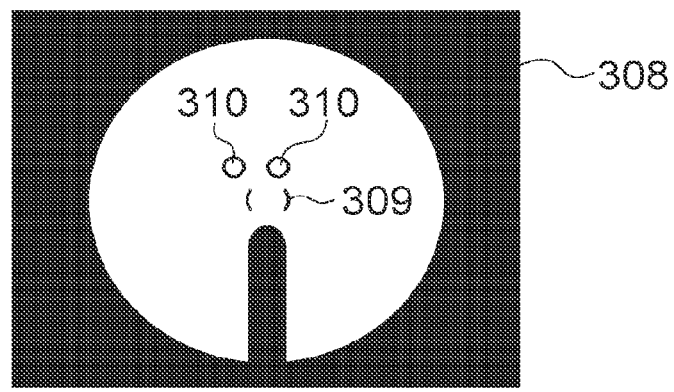
FIG. 8A is a schematic view showing an example of a display screen in the embodiment of the ophthalmological apparatus in accordance with the present invention.
Figure 8B:
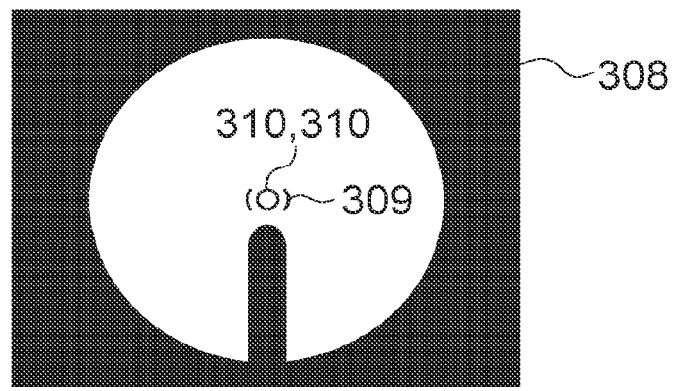
FIG. 8B is a schematic view showing an example of a display screen in the embodiment of the ophthalmological apparatus in accordance with the present invention.

With reference to FIGS. 8A and 8B, a first display example will be described. FIGS. 8A and 8B show an example of a display screen to be used for alignment adjustment. This display screen corresponds to a display screen displayed in the display 240A. While not shown, an observation image (a fundus image of the subject's eye E) acquired by the fundus camera unit 2 is displayed in the display screen shown in FIGS. 8A and 8B.

In FIGS. 8A and 8B, an alignment reference position mark (parentheses mark) 309 is displayed at a reference position in a display screen 308. The reference position means a central position of the observation image. The alignment reference position mark 309 is an image showing a position of a moving target of pseudo alignment index images 310. The display screen 308 displays the two pseudo alignment index images 310 and 310. A display position of each of the two pseudo alignment index images 310 and 310 changes in accordance with information on positional displacement of the optical system for inspection with respect to the subject's eye E. That is, the control unit 210 controls the display position of each of the two pseudo alignment index images 310 and 310 in accordance with displacement (an amount and direction of positional displacement) of the optical system for inspection with respect to the subject's eye E in each of the x-direction (side-to-side direction), the y-direction (vertical direction), and the z-direction (direction of working distance).

For example, if the optical system for inspection is displaced in the xy-directions with respect to the subject's eye E, as shown in FIG. 8A, the pseudo alignment index image 310 is displayed at a position away from the alignment reference position mark 309. In addition, if the optical system for inspection is displaced in the z-direction with respect to the subject's eye E, as shown in FIG. 8A, each of the two pseudo alignment index images 310 and 310 is displayed away from each other at a predetermined interval. Meanwhile, if alignment in all the xyz-directions is proper, as shown in FIG. 8B, the pseudo alignment index images 310 and 310 are displayed inside the alignment reference position mark 309 while superimposed with each other.

That is, a display position of each of the pseudo alignment index images 310 and 310 with respect to the alignment reference position mark 309 is controlled so as to change in accordance with displacement of the optical system for inspection in the xy-directions with respect to the subject's eye E (an amount and direction of positional displacement in the xy-directions from a proper position). In addition, an interval (distance) between the pseudo alignment index images 310 and 310 displayed is controlled so as to change in accordance with displacement of the optical system for inspection in the z-direction with respect to the subject's eye E (an amount of positional displacement in the z-direction from the proper position).

According to the display example described above, it is possible to manually perform alignment adjustment while an observation image (a fundus image of the subject's eye E) displayed in a screen of the display 240A is observed with a familiar operational feeling.

In this embodiment, since the pseudo alignment index image is displayed in a pseudo manner, it is possible to always display the alignment reference position mark at a predetermined reference position regardless of change of an inspection portion (or a projection position of a vision fixation target). Accordingly, for example, even if a fundus peripheral portion is selected as an inspection portion, there is less possibility that an alignment index image is eliminated in a screen of a display, as compared with a conventional ophthalmological apparatus. As a result, it is possible to smoothly perform alignment adjustment on the basis of quantitative information without depending on experience and proficiency of a user.

S11: Implementation of Manual Alignment

The user performs predetermined operation using the operation unit 240B to move the optical system for inspection while observing the observation image displayed and checking the pseudo alignment index image.

At this time, the control unit 210 enables a display position of the pseudo alignment index image to be changed in accordance with contents of movement of the optical system for inspection. For example, the control unit 210 acquires information on positional displacement in real time again in accordance with the contents of movement of the optical system for inspection to update a display of the pseudo alignment index image in real time in accordance with the newly-acquired information on positional displacement.

In addition, the control unit 210 determines whether positional displacement in all the xyz-directions of the optical system for inspection with respect to the subject's eye E is within a predetermined allowable range or not. If it is determined that the positional displacement is within the allowable range, a pseudo alignment index image may be displayed in a display form different from that in a case where the positional displacement is out of the allowable range.

In a case where it is determined that the positional displacement is within the allowable range, an aspect of changing a display form of each of the two pseudo alignment index images is not limited to the example described above, and thus others except a color, such as a size, a shape, and a blinking pattern, may be changed, and a combination thereof may be available. In addition, any visually discriminable form, such as a pattern, brightness, density, and transparency, is available.

Referring to information on the subject's eye enables correctness of manual alignment to be further improved. The information on the subject's eye, for example, is measurement information showing characteristics of the subject's eye acquired by an inspection previously performed with respect to the subject's eye E. The measurement information may be acquired by the ophthalmological apparatus or another ophthalmological apparatus. Then, the measurement information is previously stored in the storage unit 212 by being associated with a patient ID, and the like.

The control unit 210 selects the measurement information corresponding to the subject's eye E on the basis of the patient ID, and the like. In addition, the control unit 210 creates information on positional displacement on the basis of the measurement information selected and the three-dimensional position of the subject's eye E acquired by the analysis unit 231. An example of this processing enables information on positional displacement (amount and direction of positional displacement) in the x-direction and the y-direction to be corrected on the basis of a deviation of a cornea shape. In addition, it is possible to correct information on positional displacement (amount and direction of positional displacement) in the z-direction on the basis of eye axial length. The latter is effective particularly in a case where a fundus is inspected.

In this way, creating information on positional displacement in consideration of the measurement information of the subject's eye E enables information on positional displacement with higher correctness in accordance with an individual difference of a subject's eye to be acquired and presented.

S12: Start of Inspection

When the processing of manual alignment in step S11 is finished, the control unit 210 starts the inspection designated in step S2.

S13: Finish of Inspection

When the inspection of the subject's eye E is finished, this example of operation is finished.

Function and Effect

Function and effect of the ophthalmological apparatus 1 as described above will be described.

The ophthalmological apparatus 1 includes the photographing mode selection unit 2401, the photographic optical system 30, the vision fixation optical system, and the control unit 210. The photographing mode selection unit 2401 selects any one of a plurality of photographing modes including the color photographing mode and the fluorescent photographing mode. The photographic optical system 30 photographs the subject's eye E in a photographing mode selected by the photographing mode selection unit 2401. The vision fixation optical system includes the LCD 39 that displays a vision fixation target, and projects an image of the vision fixation target displayed in the LCD 39 on the subject's eye E. The control unit 210 changes the amount of light of the vision fixation target in accordance with the photographing mode selected by the photographing mode selection unit 2401.

The ophthalmological apparatus 1 described above changes the amount of light of the vision fixation target in accordance with a photographing mode selected from among the plurality of photographing modes including the color photographing mode and the fluorescent photographing mode. Accordingly, for example, if the fluorescent photographing mode is selected, the amount of light of the vision fixation target can be automatically increased, thereby enabling fluorescent photographing to be performed in a stable state without deteriorating visibility of the vision fixation target. In addition, if the color photographing mode is selected, the amount of light of the vision fixation target is reduced as compared with a case where the fluorescent photographing mode is selected to enable color photographing to be performed in a desired state without causing miosis of the subject's eye E. Thus, it is possible to optimize vision fixation in accordance with the photographing mode.

In the embodiment described above, although the amount of light of the vision fixation target is automatically changed in accordance with the photographing mode, for example, a color or a lighting pattern (lighting/blinking) of the vision fixation target along with the amount of light of the vision fixation target may be changed according to a table shown in FIG. 9, as another configuration. Accordingly, as compared with the embodiment described above (an aspect of controlling only the amount of light of the vision fixation target), variety can be applied to visibility of the vision fixation target in accordance with a photographing mode because the vision fixation target is displayed in a state where not only the amount of light but also a color and a blinking pattern are combined. As a result, it is possible to perform photographing in a more desirable state.

Although the amount of light of the vision fixation target, a color, and a lighting pattern (lighting/blinking), corresponding to each of the photographing modes, are previously set in a table, a user may change these setting values through a setting menu (not shown).

Figure 10:
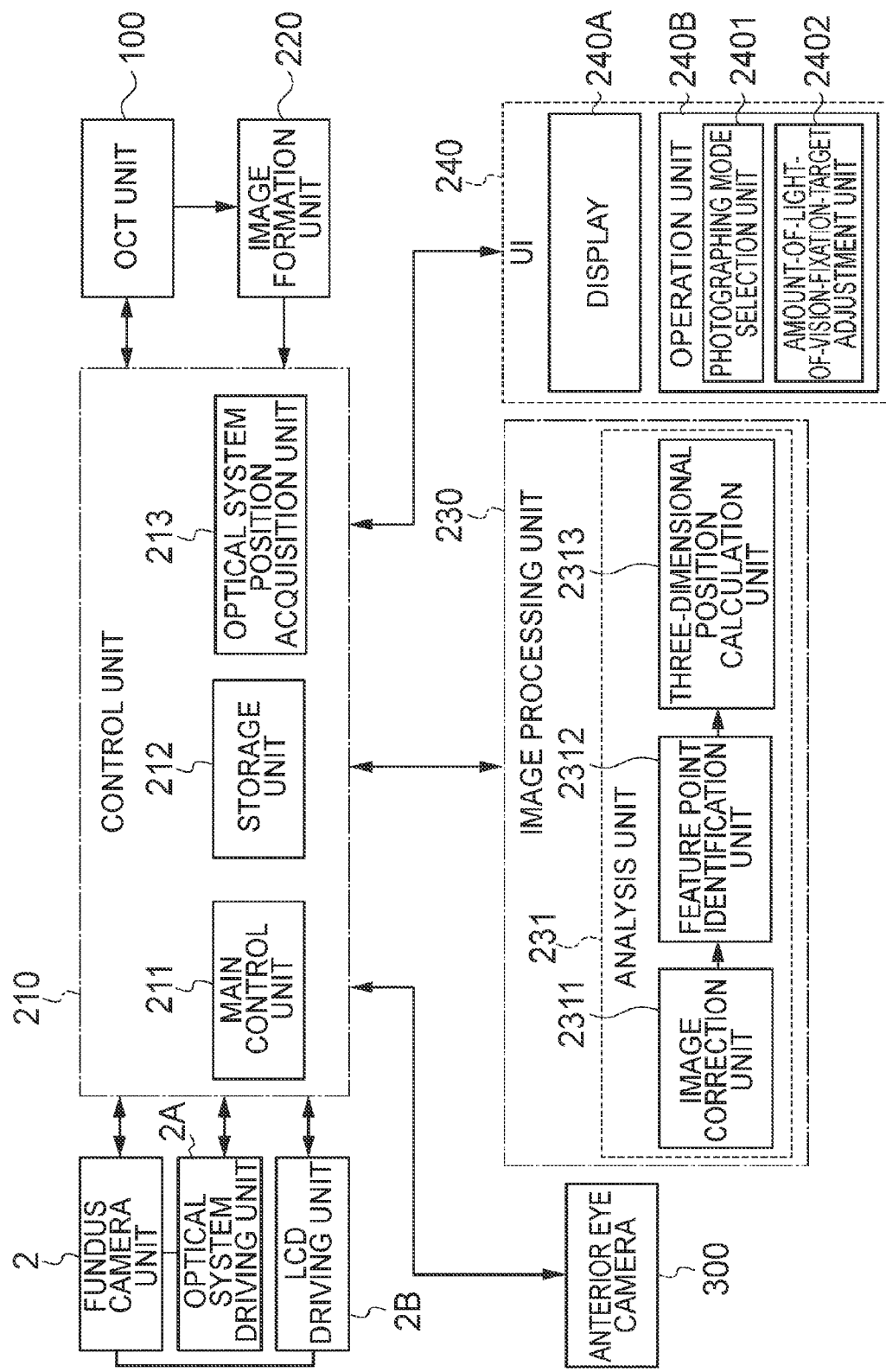
FIG. 10 is a schematic block diagram view showing another example of a configuration of a control system of the embodiment of the ophthalmological apparatus in accordance with the present invention.

As another configuration example, the amount of light of the vision fixation target is not only automatically changed in accordance with a photographing mode, but also may be manually changed if necessary. For example, as shown in FIG. 10, the operation unit 240B includes an amount-oflight-of-vision-fixation-target adjustment unit 2402 so that the amount of light of the vision fixation target can be manually changed by operating the amount-of-light-of-vision-fixation-target adjustment unit 2402. Accordingly, since a user is able to perform fine adjustment of the amount of light of the vision fixation target according to an inspection state and the like, it is possible to optimize vision fixation in a more preferable state.

Figure 11:
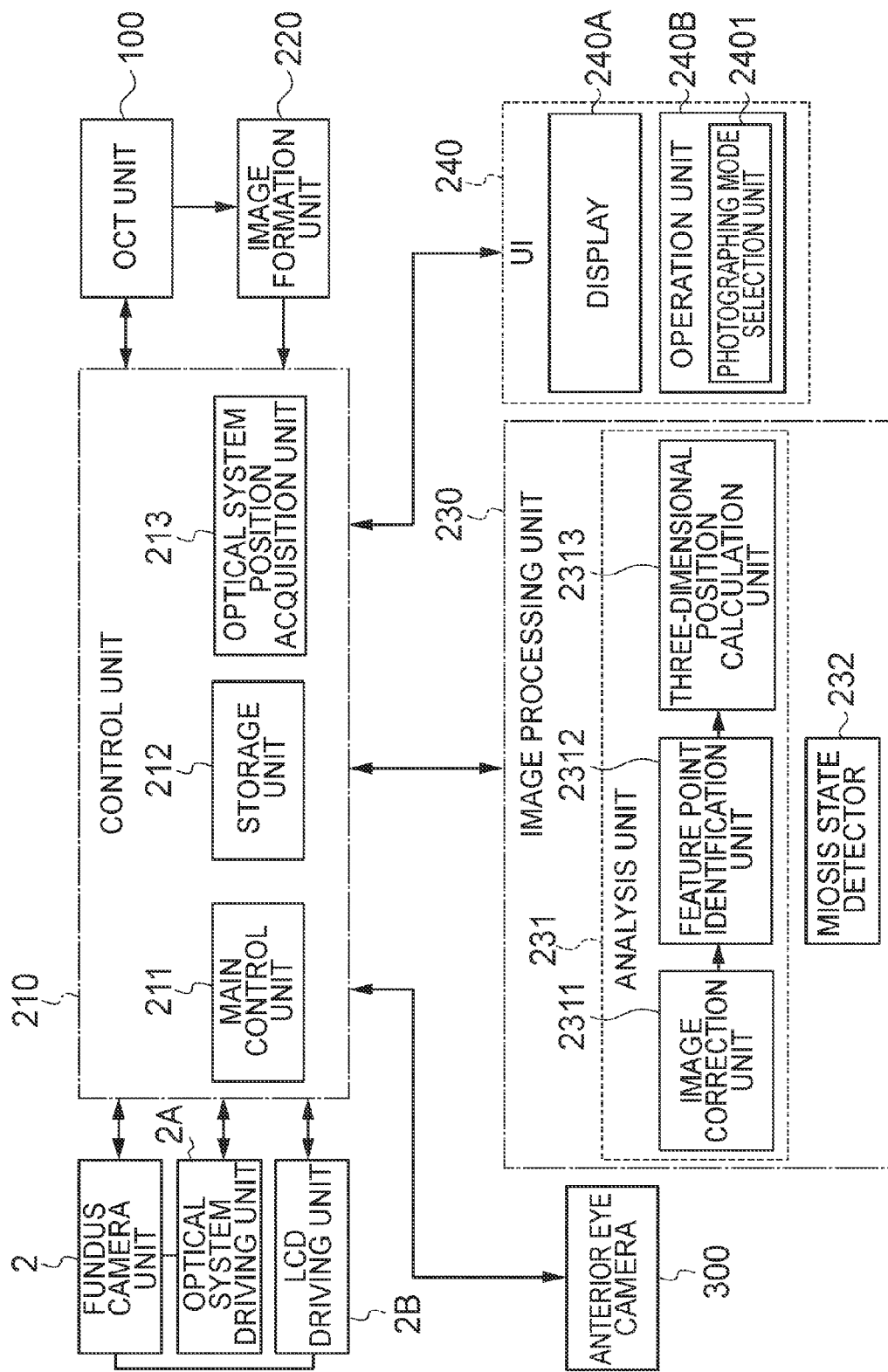
FIG. 11 is a schematic block diagram view showing another example of a configuration of a control system of the embodiment of the ophthalmological apparatus in accordance with the present invention.

In addition, as another example of a configuration, it is preferable that the image processing unit 230 includes a miosis state detector 232 that detects whether there is miosis of the subjects eye Eon the basis of an image photographed by the photographic optical system 30, as shown in FIG. 11. In this case, the control unit 210 controls the amount of light of the vision fixation target to be reduced if the miosis state detector 232 detects miosis of the subject's eye E. Accordingly, it is possible to prevent miosis of the subject's eye E caused by influence of the amount of light (brightness) of the vision fixation target from occurring during observation before the subject's eye E is photographed in each of the photographing modes, thereby enabling photographing to be performed in a proper state. The miosis state detector 232 corresponds to an example of the "detector".

Modification

The configurations described above are only an example of suitably practicing the present invention. Thus, any modification (such as elimination, replacement, and addition) within the scope of the gist of the present invention is appropriately applicable.

The anterior eye camera 300 (photographing unit) may be arranged below a lens center of the objective lens 22 (−y-direction). Accordingly, it is possible to reduce a possibility that an eyelid or eyelashes of a subject may be displayed in a photographed image acquired by the anterior eye camera 300 (photographing unit). Thus, even if a subject has a deep hollow of the eye (orbit), it is possible to suitably perform anterior eye photographing.

The embodiment described above enables the image processing unit 230 to combine two photographed images that are substantially simultaneously acquired by the anterior eye cameras 300A and 300B to allow the composite image to be displayed. Accordingly, it is possible to observe a three-dimensional form of the anterior eye Ea. It is also possible to perform the analysis processing of the embodiment described above by using the composite image.

In the embodiment described above, the control unit 210 is capable of allowing at least one of two photographed images that are substantially simultaneously acquired by the anterior eye cameras 300A and 300B to be displayed. Accordingly, it is possible to observe a form of the anterior eye Ea from different visual points (photographing positions).

The anterior eye camera 300 may be attached to a front face of the body 420, or stored in the body 420. That is, the anterior eye camera 300 may be arranged so as to project from the front face of the body 420, or arranged so as to be substantially in flush with the front face of the body 420. The anterior eye camera 300 may be also provided so as to be arranged at a recessed position with respect to the front face of the body 420 from the front face.

In a case where the anterior eye camera 300A is provided so as not to project from the front face of the body 420, following advantages can be acquired: causing no obstruction to eyelid opening or external vision fixation operation, and avoiding failure of acquiring positional information due to vignetting of an image itself.

It is also possible to provide the anterior eye camera 300 at a position other than the front face of the body 420. For example, the anterior eye camera 300 may be provided at a position in a side face of the body 420, as well as an optical system (such as a mirror) that changes a direction of an optical axis of the anterior eye camera 300 to guide light into the subject's eye E may also be provided. In addition, the anterior eye camera 300 may be provided in the body 420, as well as the same optical system may also be provided. If this kind of optical system is provided, it is perceived that providing the anterior eye camera 300 and the optical system in the body 420 is desirable in consideration of disturbance with respect to anterior eye photographing. In that case, it is perceived that applying a configuration in which the anterior eye camera 300 and an optical system are separated from another optical system to avoid influence on anterior eye photographing by another optical system (such as an optical system for inspection) is desirable. For separation of the optical system, an optical path separation member, such as a prism, and a dichroic mirror, is available.

In the embodiment described above, while a position of the optical path length change unit 41 is changed to change a difference in length between an optical path of the signal light LS and an optical path of the reference light LR, a method of changing the difference in the optical path length is not limited to this. For example, a reflection mirror (reference mirror) is arranged in an optical path of reference light, and then the reference mirror is moved in a direction of travel of the reference light to change optical path length of the reference light, thereby enabling a difference in the optical path length to be changed. In addition, the fundus camera unit 2 and the OCT unit 100 may be moved with respect to the subject's eye E to change optical path length of the signal light LS, thereby changing a difference in the optical path length.

It is possible to store a computer program for achieving the embodiment described above in any non-transitory computer-readable tangible medium readable by a computer. For this medium, for example, a semiconductor memory, an optical disk, a magneto-optical disk (such as a CD-ROM, a DVD-RAM, a DVD-ROM, and an MO), a magnetism recording medium (such as a hard disk, a floppy (registered trademark) disk, and ZIP), and the like, are available.

It is also possible to transmit and receive the program through a network, such as the Internet, and a LAN.

What is claimed is:

1. An ophthalmological apparatus comprising:
   a photographing mode selection processor that selects any one of a plurality of photographing modes including a color photographing mode and a fluorescent photographing mode;
   a photographic optical system that photographs a subject's eye in a photographing mode selected by the photographing mode selection processor;
   a vision fixation optical system including a vision fixation target display that displays a vision fixation target, the vision fixation optical system projecting an image of the vision fixation target displayed in the vision fixation target display on the subject's eye; and
   a control processor that changes an amount of light of the vision fixation target in accordance with the photographing mode selected by the photographing mode selection processor, wherein
   the control processor increases the amount of light of the vision fixation target in a case where the fluorescent photographing mode is selected as compared with a case where the color photographing mode is selected.

2. The ophthalmological apparatus according to claim 1, wherein the control processor changes a color of the vision fixation target in accordance with the photographing mode selected by the photographing mode selection processor.

3. The ophthalmological apparatus according to claim 2, wherein the control processor allows the vision fixation target to light or blink in accordance with the photographing mode selected by the photographing mode selection processor.

4. The ophthalmological apparatus according to claim 2, further comprising:
   a detector that detects whether there is miosis of the subject's eye on the basis of an image photographed by the photographic optical system,
   wherein the control processor reduces the amount of light of the vision fixation target if the detector detects miosis of the subject's eye.

5. The ophthalmological apparatus according to claim 3, further comprising:
   a detector that detects whether there is miosis of the subject's eye on the basis of an image photographed by the photographic optical system,
   wherein the control processor reduces the amount of light of the vision fixation target if the detector detects miosis of the subject's eye.

6. The ophthalmological apparatus according to claim 1, wherein the control processor allows the vision fixation target to light or blink in accordance with the photographing mode selected by the photographing mode selection processor.

7. The ophthalmological apparatus according to claim 6, further comprising:
   a detector that detects whether there is miosis of the subject's eye on the basis of an image photographed by the photographic optical system,
   wherein the control processor reduces the amount of light of the vision fixation target if the detector detects miosis of the subject's eye.

8. The ophthalmological apparatus according to claim 1, further comprising:
   a detector that detects whether there is miosis of the subject's eye on the basis of an image photographed by the photographic optical system,
   wherein the control processor reduces the amount of light of the vision fixation target if the detector detects miosis of the subject's eye.

* * * * *